(12) United States Patent
Krespi

(10) Patent No.: US 12,201,848 B2
(45) Date of Patent: Jan. 21, 2025

(54) DEVICE AND METHODS FOR USE IN REMOVAL OF BIO-FILM AND TREATMENT OF HALITOSIS

(71) Applicant: Yosef Krespi, New York, NY (US)

(72) Inventor: Yosef Krespi, New York, NY (US)

( * ) Notice: Subject to any disclaimer, the term of this patent is extended or adjusted under 35 U.S.C. 154(b) by 0 days.

(21) Appl. No.: 15/666,566

(22) Filed: Aug. 2, 2017

(65) Prior Publication Data

US 2018/0036554 A1 Feb. 8, 2018

Related U.S. Application Data

(60) Provisional application No. 62/370,696, filed on Aug. 3, 2016.

(51) Int. Cl.
*A61N 5/00* (2006.01)
*A61N 5/02* (2006.01)
(Continued)

(52) U.S. Cl.
CPC .......... *A61N 5/0624* (2013.01); *A61N 5/022* (2013.01); *A61N 5/0603* (2013.01); *A61N 5/0625* (2013.01); *A61N 1/0548* (2013.01); *A61N 2005/0606* (2013.01); *A61N 2005/0626* (2013.01); *A61N 2005/063* (2013.01); *A61N 2005/0644* (2013.01); *A61N 2005/0651* (2013.01); *A61N 2005/0659* (2013.01); *A61N 2005/0661* (2013.01); *A61N 2005/0662* (2013.01); *A61N 5/067* (2021.08)

(58) Field of Classification Search
CPC .... A61N 2005/0644; A61N 2005/0606; A61N 5/0624; A61N 5/06; A61N 5/022; A61N 1/0548; A61N 2005/063; A61N 2005/0659; A61N 2005/0661; A61N 2005/0662; A61N 2005/067; A61B 18/26

See application file for complete search history.

(56) References Cited

U.S. PATENT DOCUMENTS 5,658,148 A * 8/1997 Neuberger ............. A61N 5/062
433/29
10,028,858 B2 * 7/2018 Deckman ................ A61F 6/144
(Continued)

FOREIGN PATENT DOCUMENTS

WO WO-2006115761 A1 * 11/2006 ............. A61B 18/22

*Primary Examiner* — Sana Sahand
(74) *Attorney, Agent, or Firm* — Joseph P. Aiena

(57) ABSTRACT

A device for removal of bio-film without cutting or injury to tissue is provided which is an elongated, thin and flexible member which encases a fiber optic piece and having a downward curved section at or near one end. The fiber optic protrudes from the end of the member and is covered by a diffuser to create a light emitting head, which can be used to direct light energy to a selected treatment site. Disclosed are safe, simple and effective broad-spectrum treatments for bio-film removal, such as halitosis and other microbial infections of the non-dental upper respiratory tract useful to treat bacterial and other microorganism species, including anaerobic bacteria. Electromagnetic radiative energy including visible, and optionally, thermal, RF and/or microwave wavelengths, is topically applied to internal surfaces of the upper respiratory tract to destroy or incapacitate superficial microorganisms without the use of antibiotics.

16 Claims, 7 Drawing Sheets

(51) Int. Cl.
*A61N 5/06*   (2006.01)
*A61N 1/05*   (2006.01)
*A61N 5/067*  (2006.01)

(56) References Cited

U.S. PATENT DOCUMENTS

| | | | |
|---|---|---|---|
| 2003/0170586 A1* | 9/2003 | Cozean | A61N 5/0603 433/29 |
| 2006/0007329 A1* | 1/2006 | Panicacci | H04N 1/409 348/241 |
| 2006/0167531 A1* | 7/2006 | Gertner | A61N 5/0603 607/86 |
| 2006/0178674 A1* | 8/2006 | McIntyre | A61B 18/22 606/108 |
| 2007/0027443 A1* | 2/2007 | Rose | A61C 1/088 606/16 |
| 2007/0260231 A1* | 11/2007 | Rose | A61N 5/0603 606/13 |
| 2008/0082045 A1* | 4/2008 | Goldfarb | A61B 1/00126 604/96.01 |
| 2009/0191504 A1* | 7/2009 | Mannino | A61B 5/0088 433/29 |
| 2010/0160838 A1* | 6/2010 | Krespi | A61B 18/26 601/15 |
| 2010/0239998 A1* | 9/2010 | Snyder | A61C 17/02 433/29 |
| 2011/0229841 A1* | 9/2011 | Hamada | A61N 5/0603 433/29 |
| 2015/0030989 A1* | 1/2015 | Soukos | A61N 5/0603 433/29 |
| 2015/0182283 A1* | 7/2015 | Boutoussov | A61B 18/22 606/18 |
| 2016/0067149 A1* | 3/2016 | Kishen | A61K 6/0035 433/224 |
| 2016/0158284 A1* | 6/2016 | Kalmeta | A61K 8/368 433/32 |
| 2017/0035506 A1* | 2/2017 | Waclawik | A61B 18/20 |
| 2017/0215988 A1* | 8/2017 | Gregg, II | A61C 1/0046 |
| 2018/0369609 A1* | 12/2018 | Wilder Smith | A61N 5/0624 |

* cited by examiner

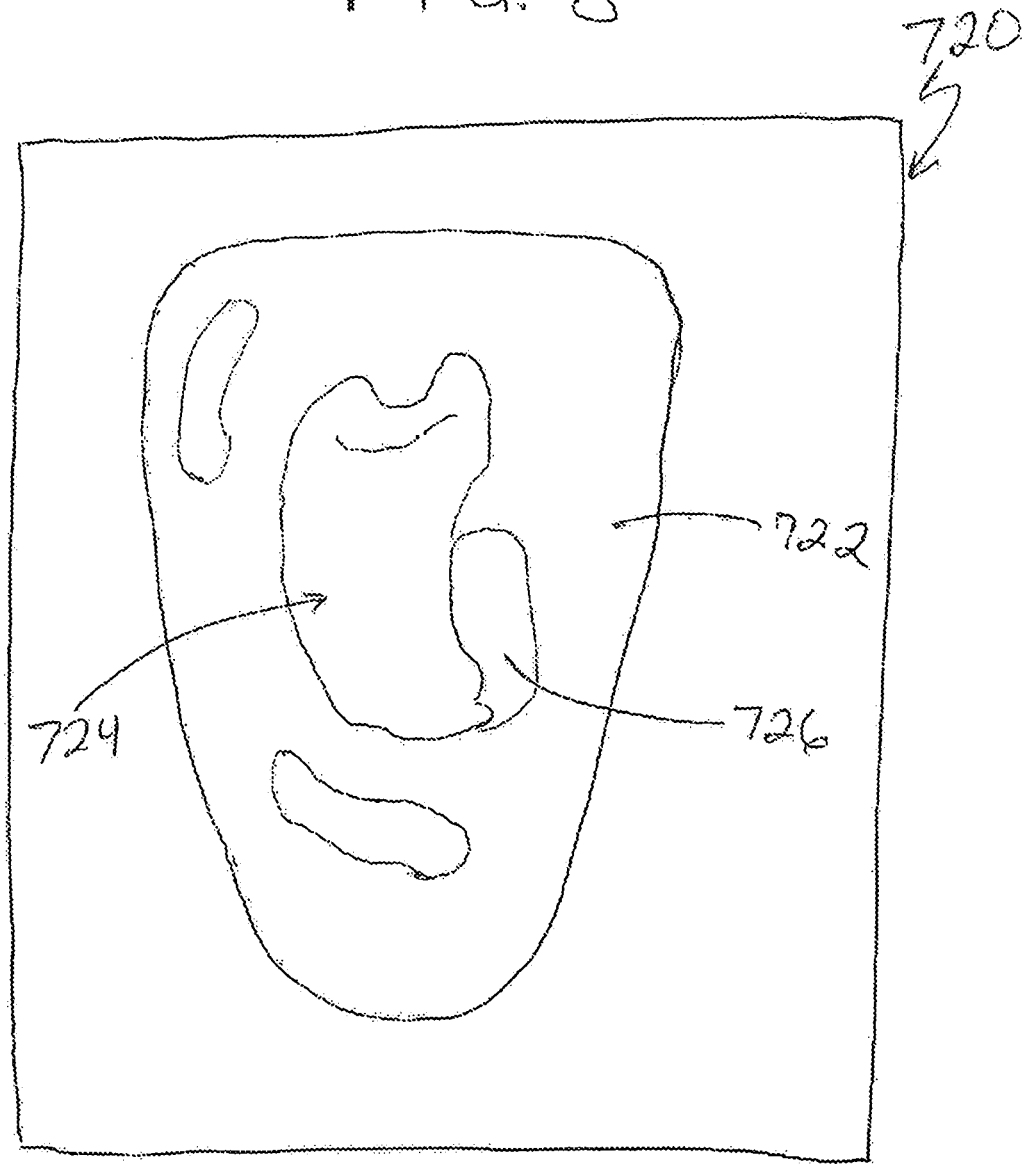

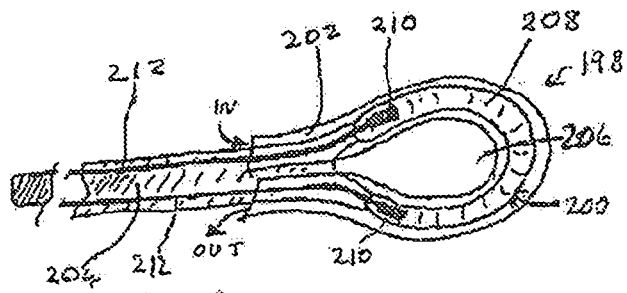
FIG. 9
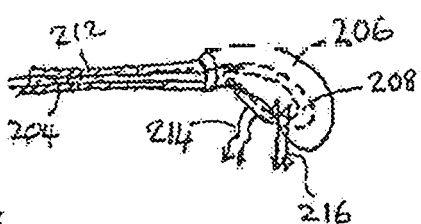
FIG. 11
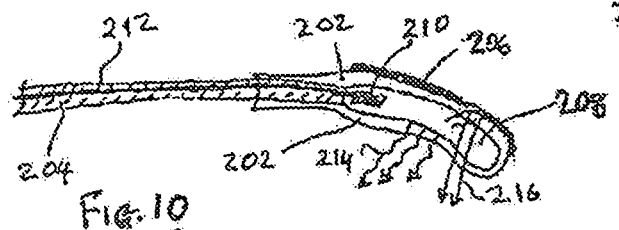
FIG. 10
FIG. 12
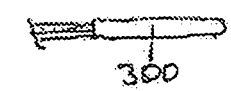
FIG. 14
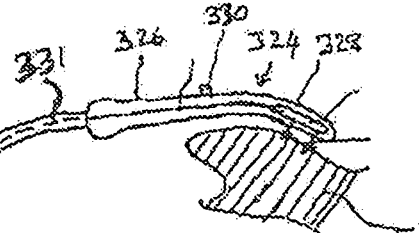
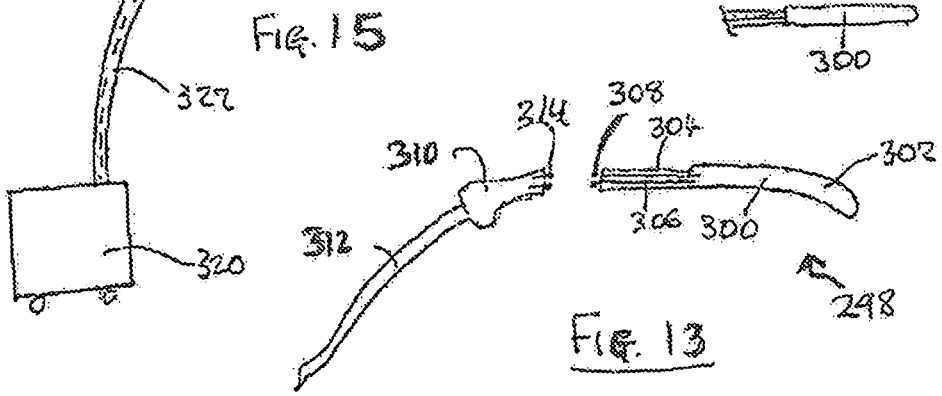
FIG. 15
FIG. 13

DEVICE AND METHODS FOR USE IN REMOVAL OF BIO-FILM AND TREATMENT OF HALITOSIS

CROSS REFERENCE TO RELATED APPLICATIONS

This application claims benefit of and priority to U.S. Provisional Application Ser. No. 62/370,696 filed on Aug. 3, 2016, and which is incorporated by reference herein in its entirety.

FIELD OF THE INVENTION

The present invention relates to an instrument for the removal of bio-film, particularly with respect to halitosis generating microorganisms, and methods of using the device in treatments, as well as diagnostic and treatment protocol for ongoing oral care.

BACKGROUND

Many people suffer persistent chronic halitosis, being bad or malodorous breath, which can often be diagnosed as being attributable to resilient colonies of bacteria that have become established in posterior oral locations such as the back of the tongue and the tonsils. As is well known, the affliction of halitosis (bad breath) may constitute a serious problem, particularly in social situations. Halitosis can be quite severe and it may occur occasionally or chronically or regularly, for example at specific times of the day or month.

Studies on the etiologies of breath malodor indicate that volatile sulfur compounds ("VSCs") which have unpleasant odors, even in extremely low concentrations, are the principal odorants in bad breath. Some examples of such VSCs are hydrogen sulfide, mercaptans, methyl mercaptan, dimethyl sulfides, skatole, cadaverine, putrescine and isovaleric acid. Such volatile sulfur compounds may originate from the anaerobic bacterial degradation, notably by anaerobic Gram-negative bacteria, of sulfur-containing amino acids within the oral cavity. Improved devices and methods of using the devices in the effective treatment of halitosis and bio-film removal are desired.

SUMMARY OF THE INVENTION

The device of the present invention for removal of bio-film without cutting or injury to tissue includes an elongated, relatively thin, and flexible member having a first end and a second end with a downward curved section approaching the second end. The first end of the thin elongated piece is connected to and inserted into to a fastener attachment at a first end of the fastener attachment and a second end of the fastener attachment has a second end for connection to a handle grip and receiving an energy supply from commercially available systems. The elongated flexible member is a hollow sheath encasing a fiber optic piece for the length of the elongated flexible member.

A fiber optic tip of the fiber optic piece protrudes from the second end of the elongated flexible member from which the treatment light energy emits. The fiber optic tip enclosed in a hollow diffuser piece fastened onto the second end of the elongated flexible member to form a light output head of the device. The diffuser piece allows light energy to emit from an open bottom of the diffuser piece and delivers visible light energy to non-dental target tissue site. The non-dental target site selected from the group consisting of the back of the tongue, a tonsil, multiple tonsils, sinus area, the throat and pharynx of a subject presented with a symptom of undesired bio-film, the target site may be determined to harbor a colony of anaerobic microorganisms generating malodorous gas wherein the visible light energy is applied to the target site at a wavelength and an intensity and for a duration effective to control the colony of microorganisms; and applying to the target site longer wavelength energy comprising heat, RF or microwave energy or combinations of two or more of the mentioned energies.

The present invention provides, in one aspect, a device and method of controlling microorganisms infecting the non-dental upper respiratory tract comprising applying electromagnetic energy to infected mucous tissues at a target site the non-dental upper respiratory tract in a manner effective to obtain a desired control of the microorganisms wherein the electromagnetic energy is pulsed and comprises light and optionally longer wavelength energy. If employed, the longer wavelength energy can, for example, comprise radiant heat, RF or microwave energy, combinations of two or more of same, or other suitable energy flux.

The electromagnetic energy desirably is chosen to be suitable for repeated use over weeks or months to treat chronic tonsillar, rhinal, sinal and other respiratory tract infections without inducing significant pain, discomfort or inflammation. Desirably the energy treatment should permit survival of significant proportions of commensal microorganisms. To these ends, the electromagnetic energy is preferably nonionizing and includes one or more energy peaks in the visible spectrum. The electromagnetic energy can comprise laser energy with a characteristic frequency in the visible or near-infrared spectrum pulses of photothermal energy rich in blue light wherein at least 70 percent of the pulse energy in the visible spectrum is polychromatic and is contained in a blue-green waveband of from about 400 to about 600 nm or from about 400 to about 500 nm. Near infrared lasers in the range of 2600 to 3000 nanometers are also used.

Alternatively the electromagnetic energy can comprise pulses of photothermal energy wherein the light energy in the visible spectrum is orange or red. Individual treatments can comprise separate applications of one or more pulses of such blue or blue-green light and such orange or red light. The electromagnetic energy can have a pulse width of not more than about 200 msec and an interval between pulses of from about 10 to about 2000 msec. Laser pulses and water and air are sent to the surface to be treated, such as the surface of a tongue, to power wash the affected area by providing a disruption or shock wave. The power wash by laser pulses, water and air has a plasma effect with cavitation occurring on the surface. To obtain this plasma effect, there is a need for moisture present from the live tissue, or water or gels that are applied to the area.

The energy application can be performed from one to five times per week for a period of from about two to about sixteen weeks and can be controlled to apply sufficient photothermal energy to effect a microorganism count reduction of at least about 80 percent. In one embodiment the energy application is effected to raise the temperature of the target tissue to from about 50.degree. C. to about 70.degree. C.

In another aspect, the invention provides a method for the treatment of halitosis comprising applying light energy to a tonsillar or lingual location determined to harbor a colony of microorganisms generating malodorous gas at a wavelength and intensity and for a duration effective to control the colony of microorganisms.

The invention also provides, in a further aspect, a method and apparatus for non-ablative treatment of lingual, palatine or other tonsils, and/or other pharyngeal anatomy wherein the treatment comprises delivering optical energy to the tonsils or other anatomy in an amount which reduces the gram negative bacterial burden of the tonsils below a level which can produce sulfuric compounds at a desired level for example 200 ppb, 80 ppb or other suitable level as known or apparent to those skilled in the art in light of this disclosure.

To facilitate treatment of deeply lodged organisms located beneath tissues surfaces, the invention can include a pretreatment procedure comprising removal of superficial microflora or other detritus or both, which optionally may include a mild exfoliation of one or more outer epithelial layers.

In a still further aspect, the invention provides treatment instrument useful for the treatment of a person suffering from halitosis comprising: a) a handle gripped in proximity to the person; b) a light output head stably supported on the handle and positioned in the person's posterior oral cavity or pharynx in a location juxtaposed to a tonsil or the back of the tongue to output light to the tonsil or the back of the tongue; and c) a light source to provide light for output from the light output head; wherein the treatment instrument can be actuated to apply light from the light source to the tonsil or the back of the tongue.

BRIEF DESCRIPTION OF THE DRAWINGS

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 8 is an illustration of the software mapping application with an image of a tongue and the affected areas.

FIG. 9 is a plan view, partly in section, of a photothermal treatment device employing a distally mounted flash lamp;

FIG. 10 is a side elevation view of the photothermal treatment device of FIG. 9;

FIG. 11 is a side elevation view of another embodiment of photothermal treatment device;

FIG. 12 is a plan view of a flash lamp configuration suitable for use in a photothermal treatment device;

FIG. 13 illustrates a further embodiment of photothermal treatment device having a detachable treatment head;

FIG. 14 is a plan view of the detachable head illustrated in FIG. 13;

FIG. 15 schematically illustrates a photothermal treatment device system employed for treating the back of the tongue;

DETAILED DESCRIPTION

The following more detailed description of the invention is intended to be read in the light of, and in context with, the preceding summary and background descriptions but without being limited by the preceding descriptions.

In one aspect the invention provides an instrument and method of treating low-level infections in the non-dental cavities or regions of the upper respiratory tract, the method comprising application to target tissue in the non-dental upper respiratory tract of sufficient photothermal energy to effect a colony microorganism count reduction of at least about 50 percent. Some useful embodiments of the invention effect a microorganism count reduction of at least about 80 percent, or at least about 90 percent and such a reduction can be effected in a single treatment. The treatments may be repeated, as necessary, to control the microorganism population.

Some useful embodiments of the invention include a mechanical, chemical or other pre-treatment procedure to remove superficial microflora or other detritus or both, and to facilitate or enhance exposure of more deeply lodged organisms located beneath tissue surfaces to the electromagnetic radiation and other agents employed in the primary treatments of the invention. Desirably, the pre-treatment is performed shortly before the primary treatment.

To achieve a desired reduction in microorganism count, the treatment energy can be applied in a dosage which is a multiple of the $LD_{50}$ for a target organism, for example, a multiple in the range of about 1 to about 3 times the $LD_{50}$, for example about two times the $LD_{50}$ which will provide a reduction of 90 percent.

The photothermal energy can be produced in any suitable manner, for example by operating a flash lamp to generate a pulsed electromagnetic output comprising both visible light and thermal energy. The energy pulse or pulses produced, or flashes, can be directed to a desired target surface in any suitable manner, for example by reflecting the energy through a window in a housing. The angular divergence of the pulses can be controlled to control the depth of penetration into mucous target tissue, if desired, with wider beams penetrating less deeply, for example by suitable choice of the shape of the reflector and other light guiding surfaces between the source and the target site.

Figure 1:
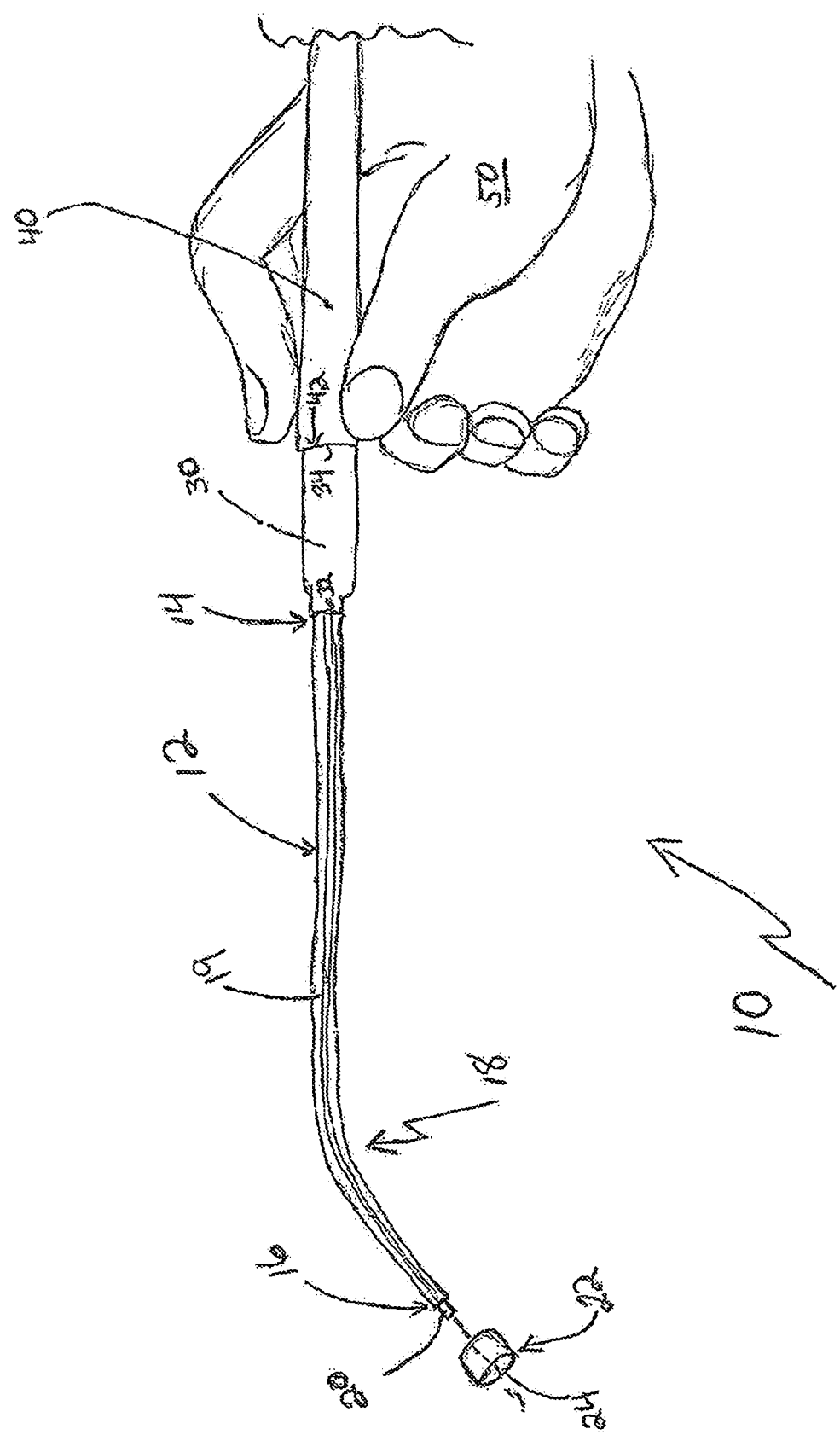
FIG. 1 is an illustration of the instrument of the present invention.

Referring to FIG. 1, there is shown the device 10 of the present invention. The instrument 10 includes a relatively thin, elongated and flexible piece 12 having a first end 14 and a second end 16 with a downward curved section 18 approaching the second end 16. The first end 14 of elongated piece 12 is connected and inserted into to a fastener attachment 30 at a first end 32 of the fastener attachment 30. At a second end 34 of the fastener attachment 30, a handle grip 40 is connected to the attachment 30 at an end 42 of the handle grip 30 by inserting the attachment 30 into the handle grip 40. The hand of a user 50 can hold the instrument 10 by use of the handle grip 40. The handle grip 40 is connected to a flexible extension which connects to commercially available hygiene and medical laser products and systems, such as those from Biolase, Inc. In this manner, the laser energy and energy for photothermal treatment travels through the hand grip 40 and fastener attachment 30 and into the fiber optic 16 contained within flexible piece 12.

The elongated piece 12 is made from any suitable rigid, but flexible material such as various metals, plastics, or composites. The elongated flexible member is a hollow sheath, capable of encasing a fiber optic piece 19 for its entire length. The thin elongated member 12 may have a length ranging from two inches to more than 12 inches. The instrument, or parts thereof, may be disposable and replaceable.

Protruding from the second end 16 of the elongated piece 12 is fiber optic tip 20, from which the treatment light or laser emits. This tip 20 is enclosed in a diffuser piece 22 which is fastened onto the second end 16 of the elongated piece 12, and together the tip 20 and diffuser 22 form a light output head of the instrument 10. The diffuser piece 22 is hollow and allows the light and the laser to emit from the bottom 24 of the diffuser piece 22. The diffuser 22, which covers the tip 20 and delivers laser energy to tissue surfaces may be various shapes and sizes, such cylindrical or spherical or other geometric shape. Various light attachments may be included as well for the diffuser. A lens may also be placed on the tip 20 where the diffuser is shown in FIG. 1. The lens enables for larger spot size of light on the tissue to be treated, with a range of approximately 0.5 millimeters to 4 millimeters in dimension. Any shape for energy delivery (circles, ellipses, squares etc.) for surface area. The shapes may be selected to deliver focused laser energy. For example, an approximate 2 to 2.5 millimeters in size circle may be used to cover the tongue surface with energy.

Figure 2:
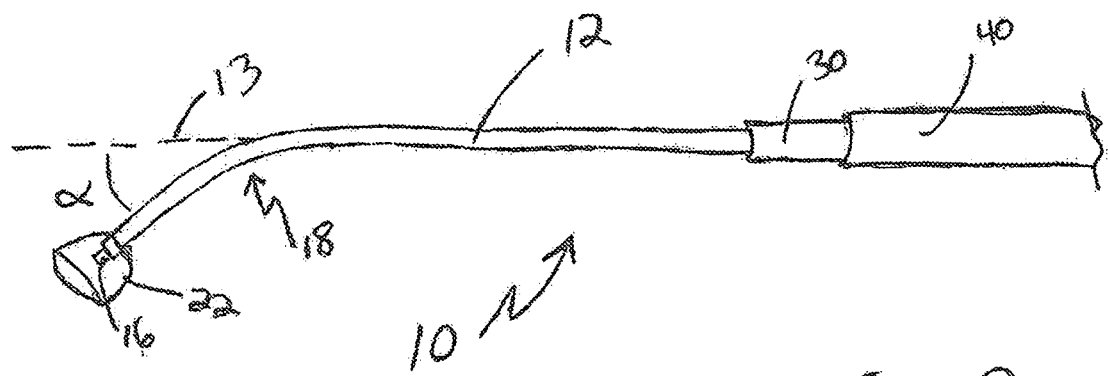
FIG. 2 is an illustration of the present invention with diffuser attached.
Figure 3:
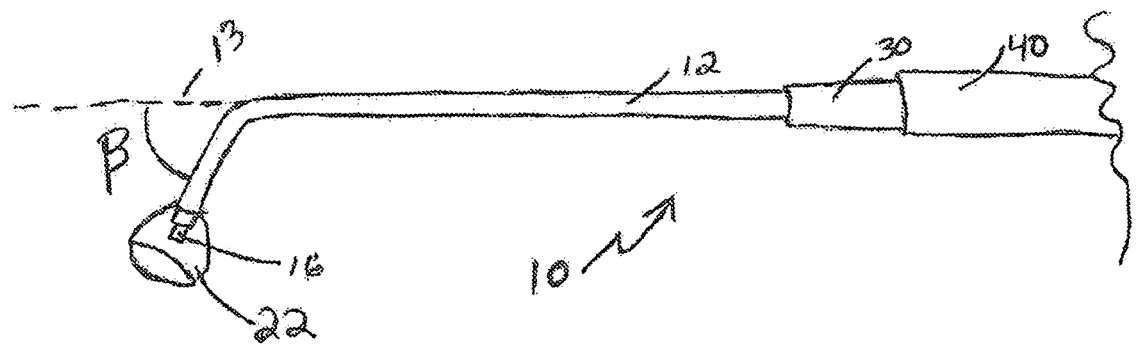
FIG. 3 is an illustration indicating the flexibility of the device.

As shown by FIG. 2, the downward curved section 18 is bent at angle from the axial plane 13 of the elongated piece 12, which may be selected from 0 degrees to 90 degrees from the plane. Angles of approximately 30 degrees to 45 degrees from the axial plane are preferred. The diffuser 22 attached to the elongated piece 12 allows laser energy to be directed from the protruding fiber tip 16 to a desired location on a surface. By having a flexible piece 12 which can be bent at various angles and curvatures 18, the instrument of the present invention can be manipulated for individual patients by the user as well as for particular treatment locations and surfaces for each patient. This is shown in FIG. 3, where the downward curved section 18 is bent at a second angle (different than the angle in FIG. 2) from the axial plane 13 of the elongated piece 12. This allows the laser energy to be directed at a second location for treatment or even adjusting for an individual patient's anatomy. The length and location of the curved section of the elongated piece 12 may be altered by bending the piece 12 at a different location. The flexibility and adjustability of the instrument allows for ease of treatment in bio-film removal.

Figure 4:
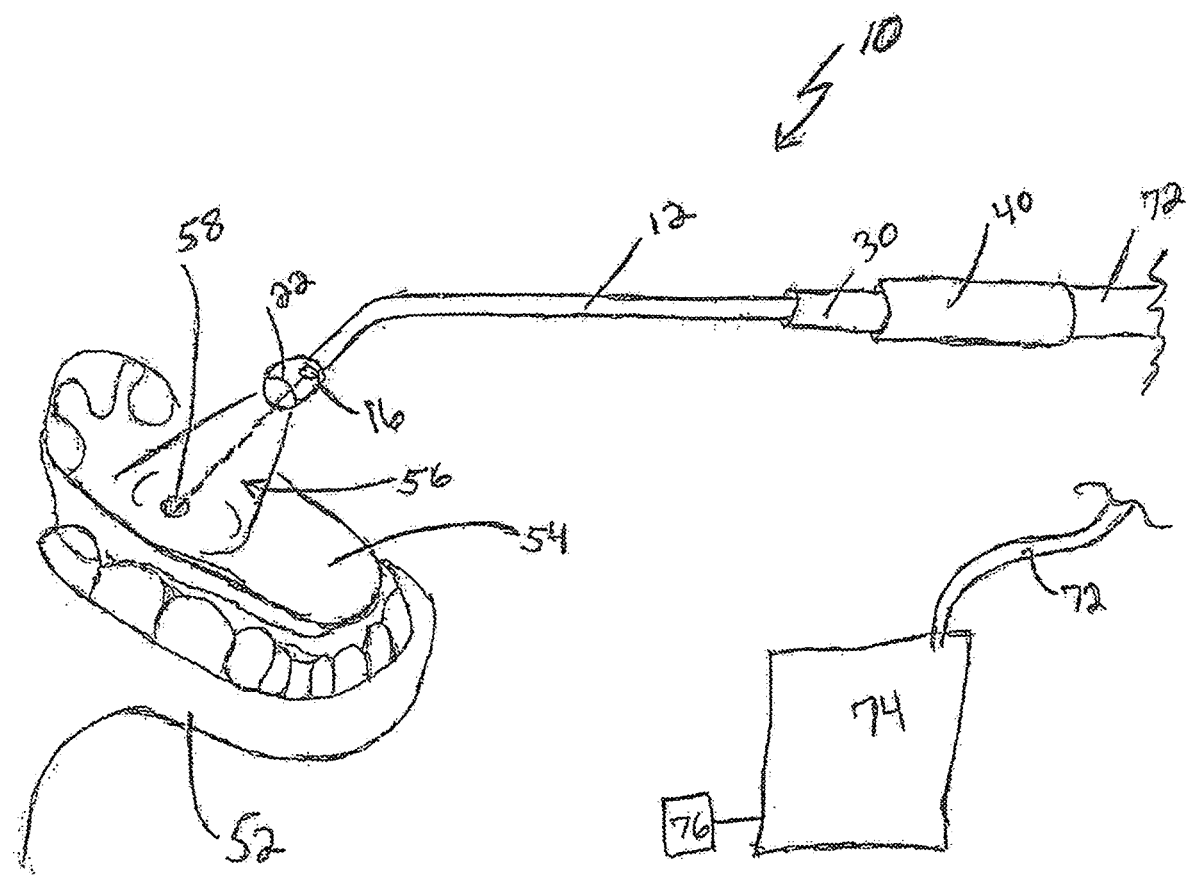
FIG. 4 illustrates the device of the present invention in use on a tissue surface of an oral cavity of a patient.

Referring to FIG. 4, there is shown the instrument of the present invention 10 in use on a tissue surface 54 for removal of bio-film from the surface 54 of a patient 52. The tissue surface may include areas such as a tongue, tonsils, sinus cavity, or pharynx. As shown in the FIG. 4, the present invention 10 is connected to commercial laser system 74 and power source 76 by the flexible extension 72 which connects into hand grip 40 so that laser energy (or energy sources described more fully below) can be delivered through handgrip 40, fastener attachment 30, the flexible elongated piece 12 and emit from the fiber optic tip 16. The laser energy and light travels through diffuser 22 and in so doing, creates an illuminated area 56 to visually assist in diagnosing the surface 54 and focusing the laser energy. The concentration of laser energy is focused at a particular selected location 58 on the tissue surface 54. The energy concentration on location 58 treats the tissue to remove bio-film without cutting or injury to the skin. By moving the instrument 10, the laser energy may be directed to other selected locations on the surface 54.

The instrument 10 of the present invention is particularly suited for cleaning bio-film from the surfaces of the tongue, tonsils, pharynx, nose and sinus cavities. There is no cutting or injury to the skin surface involved by use of the present device, and no coagulation either. By directing the laser energy onto the surfaces, bio-film can be removed, including halitosis causing bacteria from those surfaces.

The instrument 10 of the present invention is disposable and the insert/fastener attachment 30 may be replaceable as well. The fiber for use with the present invention is approximately a 200 micron fiber up to a 1000 micron fiber and the flexible piece 12 is of sufficient dimensions to encase the fiber accordingly. Lasers of up to 10 watts may be used with the present invention, although this is not limiting.

Other known methods may be included with the present invention, such as cooling the surface affected by the laser. This can be accomplished with water or cooling gels that may be spread on the surface, (anesthetics, etc.).

Energy sources. A variety of energy sources can be employed for the photothermal treatment instruments of the invention including for example pulsed light, pulsed heat and light, and continuous or pulsed LED or laser sources. If a laser is utilized, it is preferably a low intensity or relatively low intensity laser and may optionally be provided with a diffuser to spread the output radiation. Thus a laser suitable for use in the present invention can be tuned or otherwise selected to have output characteristics specifically suited to the treatment of halitosis. Desirably the output should be such as to kill a suitable percentage, e.g. 50% of target bacteria within a relatively short time period, e.g. 0.5 to 10 minutes, preferably 1 to 5 minutes, while optionally permitting survival of a useful percentage of commensal normal microorganisms. The wavelength of the laser or other light source may also be selected to target undesired rather than normal microorganisms, e.g. gram-negative bacteria. The energy system desirably outputs energy over a target area or in a target pattern which is neither a thin pencil, which would make coverage of the target difficult, nor too wide an area which could render the received radiation too weak to be effective.

One embodiment of the invention (not illustrated) employs, as an alternative to the Azar et al. light source described hereinabove, an electromagnetic energy source such as the incoherent pulsed light sources disclosed in Eckhouse et al. U.S. Pat. No. 6,514,243, the entire disclosure of which is incorporated herein by reference thereto. Eckhouse et al. employ for removal of hair from the skin by means of electromagnetic follicle destruction a gas filled flashlamp, such as a xenon-filled linear flashlamp ILC Technologies model no. L5568.

Character of Energy Output. Depending upon the nature of the organism or organisms to be controlled, the applied energy delivered from output head to the target site can be either heat energy alone or light energy alone but is preferably a mix of heat and light energy. The energy should be applied in a quantity and at a wavelength effective to obtain a desired reduction of the colony microorganism or microorganisms to be controlled. In one embodiment of the invention about 80 percent of the applied energy reaching a target site can be heat and about 20 percent can be light. These quantities can of course vary substantially and can lie in the ranges for example, of from about 60 to about 90 percent heat and about 10 to about 40 percent light.

Preferably the light energy employed includes visible wavelengths and optionally it may include a minor proportion of ultraviolet light in the wavelengths for UVA or UVB or both. However it is usually desirable to avoid UVC wavelengths which may induce DNA or other damage to human tissue. Another embodiment of the invention substantially excludes all wavelengths of ultraviolet for treatments where the potential carcinogenicity, or other potentially harmful effects of ultraviolet light are unacceptable.

While the invention is not limited by any particular theory, it is contemplated that light may often be effective to reduce superficial colonies of microorganisms at the target, i.e. microorganisms that are essentially on the surface of the target tissues. Light may also incapacitate microorganisms up to a depth of about 1 to about 1.5 mm. However, light may not adequately penetrate deeper layers of tissue harboring microorganisms, for example by being fissured or porous providing concealed volumes that may accommodate same. For example the tonsils and the tongue have deep crevices, papilla, crypts or pockets where significant populations of undesirable microorganisms may reside.

Accordingly, employment of near infrared or longer wavelength heat energy that can penetrate the superficial tissue layers and reduce microorganisms harbored in subepithelial, interestitial volumes, is contemplated as an advantageous but optional, feature of the present invention. Preferably, such heat energy is applied simultaneously with the light energy and from a common source.

By employing light energy in conjunction with mild heat energy, many microorganisms can be effectively destroyed photochemically, possibly avoiding the need to use more intense heat to raise the tissue temperature to the coagulation temperature of the microorganism. Such an embodiment of the invention can be employed where a patient has particularly sensitive, or previously damaged tissue, or there is a particular concern to avoid tissue damage. Furthermore, mild heating can increase the local blood flow, facilitating the elimination of bacteria or other microorganisms.

The applied energy can be selected to include wavelengths, in addition to visible light wavelengths, that both elevate the temperature of the target to cause thermal damage to colonies of microorganisms resident at the target and also to accelerate destructive photochemical reactions. The energy can be selected to include wavelengths absorbed by the mucous tissue at the target which is impacted by the applied radiation.

Pursuant to the invention, it is desirable to destroy microorganisms resident on or in the target tissue without damage to, or with only minimal damage to, the tissue itself and without causing the patient pain, soreness or other undesired reaction. To this end in one embodiment of the invention the tissue temperature can be raised to a temperature in the range of from about 50.degree. C. to about 70.degree. C., preferably to about 60.degree. C., for example in the range of from about 57.degree. C. to about 63.degree. C. The temperature of the target tissue can be determined in known manner or by employing a thermosensor such as thermosensor 58 carried by the photothermal treatment instrument 10 and operated during, or preferably, promptly after application of a photothermal treatment.

If desired the instrument can be calibrated by performing a number of treatments with different durations, intensities and targets and detecting the resultant target temperatures. Using this information settings and protocols can be provided for future procedures that will yield appropriate target temperatures with reasonable confidence, without the need for real time temperature determinations.

The period of elevated temperature is preferably of the order of about 1 minute for example from about 5 seconds to 5 minutes or in the range of from about 20 seconds to 2 minutes, or from about 40 to about 80 seconds. A desired period of elevated temperature may be achieved by application of one or more energy pulses, up to no more than about ten pulses within the period, each pulse being of brief duration, as described herein, and each being followed by a quiescent interval providing for tissue relaxation.

Pulsed and continuous energy flux. Some useful embodiments of the invention employ pulsed rather than continuous energy sources to provide high peak power and efficient photochemical activation of harmful chemical species in the microorganisms or in treatment materials such as oxygen gels, if the latter are employed. Other embodiments can employ continuous energy sources, if desired.

In the application of heat, use of a pulsed source can be helpful as pulsing allows for thermal relaxation of the tissue in the troughs between peaks preventing localized overheating of, and damage to, tissue.

Useful pulsed radiation for practicing the invention can have a pulse width of not more than about 200 msec, for example from about 10 to about 100 msec. In one useful embodiment of the invention the pulse width is about 25-35 msec. If multiple pulses are applied at one time, there is desirably a delay, providing a tissue relaxation interval between pulses of the order of from about 10 to about 2000 msec, desirably from about 20 to about 100 msec, for example about 40 or 50 msec, to permit tissue relaxation and prevent tissue damage.

The pulse energy delivered to the target site should be sufficient to be effective in controlling microorganisms without causing tissue damage such as to be normally perceived by the patient or that would be harmful to the patient. For example, energy pulses of from about 0.1 to about 5 J/cm.sup.2, preferably from about 0.5 to about 3.0 J/cm.sup.2 may be employed. Constant energy application may be at suitable or equivalent intensities. Useful intensities may lie in the range of from about 1 to about 1,000 milliwatts/cm.sup.2, e.g. from about 10 to about 200 milliwatts/cm.sup.2 or from about 25 to about 100 milliwatts/cm.sup.2.

If employed, the heat energy may be provided by any suitable source, for example infrared radiation, convection, conduction or in situ induction by RF or microwave energy or the like. If desired, RF or microwave energy may be applied to obtain useful therapeutic results in conjunction with light and/or a heat source. It will be understood that RF or microwave or equivalent energy fluxes can be employed to provide useful microorganism control effects by mechanisms other than local heating, for example by electroporation (cell membrane pore formation) or cell membrane rupture. Some, but not all, useful embodiments of the invention employ light, optionally in combination with another energy source.

The electromagnetic energy can be applied in any suitable wavelength mode, waveband mode or combination of wavelength and/or waveband modes which is or are effective to provide control of one or more target microorganism species without causing unacceptable pain, trauma or other side effects. A suitable source or combination of sources can be provided to generate or introduce the desired energy or energy mix in situ.

For example, any combination of two or more of light energy, heat energy, radio frequency ("RF") and microwave energy may be employed in the inventive treatments, if desired. Some useful treatment embodiments of the invention apply light energy together with heat energy and may optionally also apply RF or microwave energy. In alternative embodiments, a light energy mode is employed together with a heat energy mode, a microwave or RF mode or with a heat energy mode and a microwave or RF mode. Useful embodiments include heat energy modes wherein the heat energy is generated by RF or microwave radiation. Alternatively, the heat energy mode may comprise infrared radiation.

The invention includes embodiments wherein two or more energy modes are applied essentially simultaneously. By "essentially simultaneously" is meant that the two energy modes are applied simultaneously, or are applied in rapid succession, one after the other, such that significant cooling of the target does not occur between the first and second applications of energy.

Each energy mode source or applicator can be any suitable device as known to those skilled in the art. Combination devices and methods such as disclosed in Kreindel U.S. Pat. No. 6,702,808, the entire disclosure of which is hereby incorporated herein by this specific reference thereto, can also be employed. The invention includes novel uses of such devices and novel combinations and modifications of such devices adapting or combining them for the purposes of the invention, as will be apparent to those skilled in the art in light of the disclosure herein.

By way of example, the energy applicator device can include a light source to emit optical energy, one or more electrode pairs for generation of RF energy and/or microwave elements for generation of microwave energy. Optionally, the light source may also provide an effective intensity of heat energy. Pulsed RF energy applied by the electrodes can be applied to the target tissue either directly or through a conductive substance.

Usefully, the frequency of the RF energy can be in a range of from about 300 kHz to about 100 MHz, the output power can be from about 5 to about 200 W, pulse duration from about 1 to about 500 msec and the pulse rate can be from about 0.1 to about 10 pulse per second. Frequencies, or frequency ranges, in spectral locations assigned by governmental entities for industrial, scientific and/or medical purposes are particularly useful, including for example in the United States, FCC-assigned frequencies of about 13.56 MHz, 27.12 MHz and 40.68 MHz.

The optical energy employed with such an RF energy mode can have an intensity of from about 5 to about 100 Joules/cm2 and a pulse duration of from about 1 to 200 msec. The individual or combined energy dosages desirably are selected to avoid long-term physiological damage or unacceptable discomfort pain or other immediate adverse effects.

Visible light, if employed, may have a single wavelength, multiple wavelengths or a waveband and this or these are preferably selected according to the absorbency of the target organism or organisms, and are typically in the range of 500 to 1200 nm. Other energy modes, if employed, may also have a single wavelength, multiple wavelengths or a waveband or wavebands.

Microwave energy for use in the invention can be of any suitable frequency for example in a range of from about 100 MHz to about 50,000 MHz, the output power can be from about 0.01 to about 10 watts/ml of target volume, optionally from about 0.1 to about 2 watts/ml. Frequencies, or frequency ranges, in spectral locations assigned by governmental entities for industrial, scientific and/or medical purposes are particularly useful, including for example in the United States, FCC-assigned frequencies of about 915 MHz, 2,450 MHz, 5,800 MHz and 24,125 MHz.

Selection of a suitable energy mode or mix of energy modes to provide an effective treatment can be made on the basis of the teachings herein with the assistance of knowledge in the art, if desired. For example, useful guidance regarding antimicrobial energy treatments may be found, inter alia, in the food processing arts, for example in disclosures such as the USFDA Center for Food Safety and Applied Nutrition publication "Kinetics of Microbial Inactivation for Alternative Food Processing Technologies", dated Jun. 2, 2000, the entire disclosure of which is hereby incorporated herein by this specific reference thereto. Of particular interest is the section headed "Microwave and Radio Frequency Processing" and section 3.3 thereof.

RF and microwave energy fluxes are useful for their rapid and uniform effect and ability to penetrate subepithelially to reach microorganisms harbored in tissue crevices, folds, pockets and the like and organisms overlaid with other material, e.g. coatings or other microorganisms. Suitable guides and screens or other protective structure can be provided to introduce the desired energy flux to the target area while protecting the subject anatomy from incidental harm. The intensity and duration and other characteristics of the energy flux can be selected with these objectives in mind, without undue experimentation, and pursuant to the principles described in more detail herein for application of light or heat.

The invention includes treatment methods employing a mix of energy modes selected to provide comprehensive therapy at a target site by killing or otherwise controlling a broad spectrum of undesired microorganisms resident at the target site wherein effective energy dosages are applied so as to reach not only superficially resident microorganisms, but also deeper layers or volumes of the target site that are believed to harbor undesired microorganisms. When safely introduced to the target site, RF or microwave energy fluxes are believed useful to this end for their relatively uniform or distributed effects in solid materials especially high water solids such as tissue or other anatomical structures.

Colony count. In one embodiment of the invention, the photothermal treatment is applied in a manner such as to obtain a desired reduction of colony count of a target microorganism or microorganisms, for example a broad spectrum bacterial infection or infection by an antibiotic-resistant strain or strains of bacteria. Pursuant to this embodiment of the invention, parameters such as the intensity and spectrum of the applied energy and the duration of treatment are controlled to obtain a desired colony count reduction of the target microorganism.

The colony count reduction in a given energy dosage may for example be at least 70%, or preferably at least about 90%. A 90% reduction can generally be effected by applying twice the $LD_{50}$ for a given target organism or an average of the $LD_{50}$'s for a spectrum of target organisms. The bacterial colony count can be determined by taking a biopsy of the target site, using a scraper, swab or the like and cultivating the biopsied tissue through serial dilutions and determining the colony counts by known methods. Determinations of colony count reduction can be employed to calibrate the energy output of photothermal treatment instrument 10 to output one or more specific dosages determined to elicit a particular response in a patient or group or class of patients. Optionally photothermal treatment instrument 10 may have settable controls to provide different predetermined dosages, which controls may be labeled. For example, a duration controller may be provided for selecting the pulse duration or pulse width e.g. from about 10 to about 50 msec, and a pulse number selector may select the number of pulses output for a single actuation of photothermal treatment instrument 10, for example from 1-10 pulses, at a predetermined relaxation interval, for example of from about 10 to about 100 msec.

As described, the inventive treatments can be performed to obtain a desired temperature elevation of target tissue for a predetermined period of time or to obtain a desired microorganism colony count reduction. The treatments can also be performed to elevate the target tissue to a selected temperature or temperature range for a duration sufficient to obtain a desired colony count reduction in a target or sample microorganism or spectrum of microorganisms.

Chemical supplementation. If desired, various chemical means can be used to supplement the effect of the radiation or to sensitize the target microorganisms to the radiation. For example, the treatment may be a photochemotherapeutic treatment, for example by employing an oxygen gel or other suitable material containing a biocompatible oxidant, e.g. hydrogen peroxide, in a concentration of from about 0.5 to about 5% by weight of the gel. The oxidant chemically sensitizes the bacteria or other microorganisms to the effects of the applied radiation.

Alternatively, the target organisms may be stained, e.g. with a food dye, to enhance the absorption of light. If staining is employed the stain color can be selected to correspond with the applied light wavelengths, to enhance the effect, for example by using a blue or green stain with applied orange or red light and a red or orange stain with applied green or blue-green light.

Such gels, stains or other target treatment compositions, for example local anesthetics, can advantageously be applied employing the spacer elements constituted by brushes, if desired, or other suitable applicator as is known. For example, a local anesthetic, e.g. 4 percent XYLOCAINE (trademark), Astrazeneca LP, can be applied to the back of the tongue to suppress the gagging response, if desired, for posterior oral cavity treatments, pursuant to the invention.

Target sites. The method and instruments of the invention, employed separately or together, can be employed to treat a variety of non-dental target sites to control microorganisms infecting the target site. Suitable target sites include internal body sites located in externally opening body cavities or body cavities that are otherwise accessible without need for a catheter, for example, in the upper respiratory tract.

Dental regions of the anatomy are subject to special considerations regarding bacterial or other infections. Unique organisms may be implicated in the diseases of the teeth and the periodontal region and the distinctive nature of pathologies such as caries and gum disease render the treatment and prognosis of dental region infections to lie largely in the province of the profession of dentistry.

Figure 5:
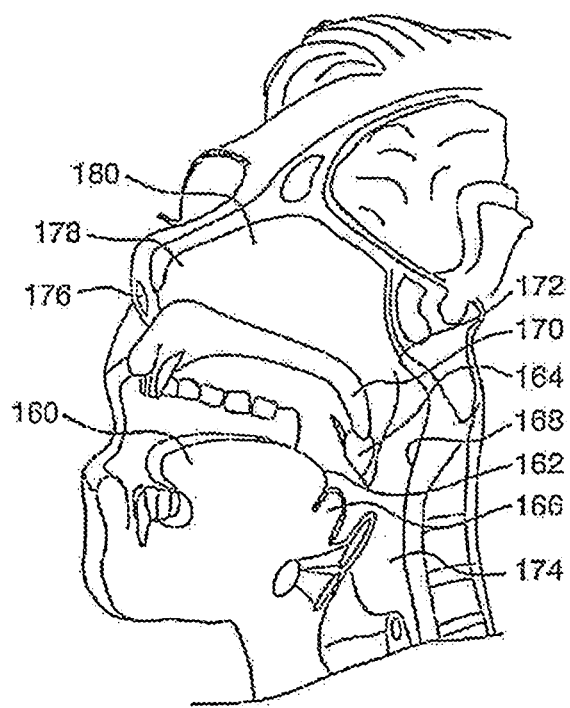
FIG. 5 is an anatomical vertical section through a human head illustrating some target treatment sites for the device and methods of the invention.

Some suitable upper respiratory tract target sites are illustrated in FIG. 5. Exemplary sites include, without limitation, the tongue 160, the back of the tongue 162, the tonsils comprising the palatine tonsils 164 (one shown), the lingual tonsil 166, the pharyngeal tonsils also called the adenoids, the pharynx 168, the uvula 170, the nasopharynx 172, the laryngopharynx 174, either or both nostrils 176 (one shown), the left or right lower nasal cavity 178 (one shown), the left or right upper nasal cavity 180 (one shown), the sinuses, especially those sinuses that are accessible via the nasal cavity and the frontal, ethmoidal, sphenoidal or maxillary sinuses. If desired substantially all the pharyngeal lymphoid tissue, including the palatine tonsils, lingual tonsils, adenoids, and pharyngeal wall lymphoid vegetation may be treated. This anatomical region is sometimes called "Waldeyer's Ring".

Figure 6:
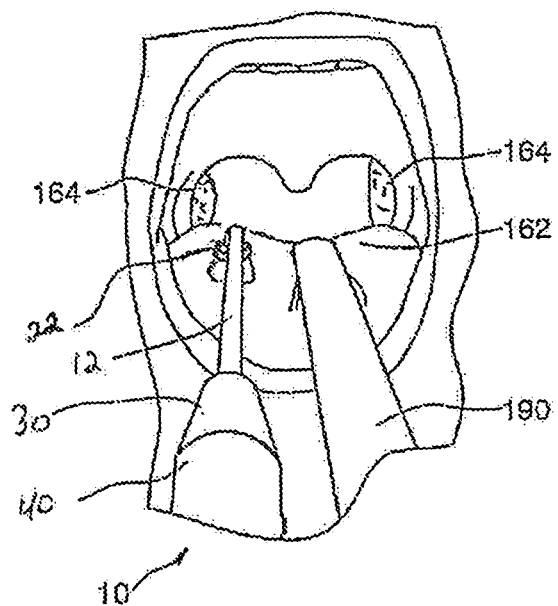
FIG. 6 is a partial view of the oral cavity of a patient during a photothermal treatment according to the invention.

Referring to FIG. 6, there is shown the present invention 10 in use on a patient's oral cavity. The individual patient's tongue 162 is held down by tongue depressor 190. Shown in the diagram is the handgrip 40, attachment piece 30 and elongated thin member 12 which surrounds and contains the fiber optic where laser energy travels. The diffuser 22 at light emitting head of instrument 10 is illustrated illuminating an area on the surface of the tongue 162, which may be the recipient of directed energy for biofilm removal and treatment. If the tonsils 164 require biofilm removal, the instrument may be moved inside oral cavity so that diffuser 22 directs light and energy.

Various suitable instruments, including the instruments described herein, for treating one or more target sites, as well as other suitable target sites, will be apparent to those skilled in the art in light of the disclosure herein.

Target conditions. Target conditions that can be treated by the methods and instruments of the invention include low-level or chronic infections of microorganisms comprising bacteria, fungi, viruses and any other microorganisms that may be present at the target site. The inventive treatments are broad spectrum and are contemplated to be active or effective against each of the foregoing classes of microorganisms. In particular the photothermal treatments of the invention are contemplated to be effective against antibiotic-resistant bacteria and anerobic bacteria. Furthermore, the treatments of the invention can be controlled to be effective against nonplaque bacteria and the invention includes treatments limited to control of nonplaque bacteria and other microorganisms. An ability to effectively treat antibiotic-resistant bacteria is especially advantageous.

Some of the conditions that can be treated include halitosis or bad breath, soreness of the tonsils or throat, stuffy or runny nose, streptococcal or other bacterial or viral infections of the posterior oral cavity and/or the pharynx, viral infections such as colds of the upper respiratory tract, influenza, sinusitis, congestion and other low-level chronic infections of the upper respiratory tract. In general, bacterial, viral, fungal, or other infections by microorganisms, of accessible surfaces, especially non-dental mucosal surfaces of the upper respiratory tract, as described above, or as otherwise apparent to those skilled in the art, can be treated by the methods and devices or instruments of the invention.

Methods of Treatment. The microorganism control treatments and instruments of the invention are particularly suited for professional use, for example for use by suitably licensed medical practitioners to treat patients in their offices. However, the invention is not so limited and can be practiced in any suitable location, including hospitals and homes. Suitable treatment protocols may vary according to the severity and persistence of the infection, the responsiveness of an individual patient and the persistence of patient-perceived symptoms. Suitable treatment protocols can comprise diagnosis of a condition and its proximate cause, an individual energy application procedure as described herein, performed on one or more infected target surfaces to a desired conclusion, such as a tissue temperature elevation or microorganism colony count reduction, repeated as infrequently as biweekly or even monthly, continued indefinitely, e.g. for two or more years, or more desirably for no more than about one year. Other desirable embodiments of the invention comprise more frequent such procedures continued for shorter periods, for example from one to five times per week, desirably once or twice per week, for periods of from about two to about sixteen weeks preferably from about four to eight weeks for example for five or six weeks.

Individual procedures can comprise one or two shots of energy applied for example to the back of the tongue and to each palatine tonsil and/or other target site. In another embodiment, a pulsed treatment is scanned across a target area in a number of individual steps. Each individual procedure can have a duration of from about 10 seconds to about 10 minutes, preferably from about 30 seconds to about 2 minutes, per target site referring to the time that a treatment instrument is disposed to direct energy toward the target surface.

Preliminary steps of the treatment procedure can comprise verifying the patient's condition, for example as being a chronic halitosis suffered, and diagnosis of a proximal cause of the condition as being an upper respiratory tract infection, for example a bacterial infection of the back of the tongue or one or more tonsils.

To perform a desired procedure on a patient to treat one of the described target conditions employing photothermal treatment instrument 10, the medical practitioner initially determines the desired energy output of the photothermal treatment instrument 10 by selecting an appropriate lamp and filter or filters. In addition, the practitioner sets controls for power output and duration of energy output to values selected to be appropriate for the target condition, if such controls are present.

The patient is prepped as necessary for example, by employing a mouthwash or gargle or other appropriate hygiene treatment, and by application of one or more desired locally acting agents to the target site or sites, for example an oxygen gel or a local anesthetic such as is conventionally used orally or in the pharynx, for example a spray of 4 percent XYLOCAINE (trademark), Astrazeneca LP.

Usefully, such prepping or pre-treatment steps may include removal of superficial microorganisms from the target areas and optionally also from the vicinity of the target areas to facilitate access of the primary treatments, for example the xenon flashlight radiation applied in Example 1, to the target organisms which may be lodged in deeper folds, crevices or fissures of tissues such as the back of the tongue and tonsils.

Superficial cleansing to remove microorganisms with or without desquamation, may be effected chemically, by applying an effective quantity of chlorhexidine or other suitable broad spectrum antibiotic. Alternatively, the pre-treatment may be effected mechanically using a suitable surgical scraping or ablation device or process, to mechanically remove superficial organisms, and possibly a layer or layers of epithelial tissue cells. For example, a simple manual scraper or brush may be employed. Alternatively a powered vibrating or oscillating scraper, brush or other suitable abrading device, optionally ultrasonic, may be employed. Carefully controlled laser ablation could be employed if desired in the pretreatment.

Both chemical and mechanical means can be employed, if desired. Gels can be used in an effective amount to retain a chemical or biochemical agent in situ for longer periods than liquid agents, if desired. Desirably, the pre-treatment can be effected without causing inflammation or pain. If desired or helpful, a local anesthetic may be applied as an initial element of the pretreatment to control pain or, if appropriate, the gagging reflex.

Desirably also the extent or degree of the pretreatment is monitored by the practitioner to determine a suitable end point, which may be indicated, for example, by the exposure of pink tissue, without reddening. Optical aids may be employed to assess tissue color if desired.

The pretreatment may be applied to any appropriate tissue or other anatomical surface to be treated or any proximate such surface, as may be determined by the medical practitioner or other user. Exemplary such surfaces include the back of the tongue the lingual, palatine or other tonsils, surfaces showing whitening or other discoloration commonly associated with the presence of abnormal microorganism populations, or surfaces from which sulfur-containing gases may emanate as determined by suitable tests.

Useful objectives of such pretreatments may be twofold: removal of undesired microfloral growths and removal of a layer or layers that may be opaque to radiation that is to be applied in the primary treatment, thereby enabling the radiation to access deeper seated organisms.

The present invention 10 may be used with the following non-limiting examples from U.S. Pat. No. 7,544,204 which is incorporated herein by reference in its entirety.

EXAMPLE 1: Treatment of Chronic Halitosis

A patient presenting with chronic halitosis is diagnosed with a bacterial infection of the tonsils and is treated, using photothermal treatment instrument 10 as shown in FIGS. 1-3, equipped with a xenon flashlight and a blue filter, transmission about 400-500 nm, with two photothermal energy pulses of about 35 msec, with a 50 msec interval, at an energy density of about 2.5 J/cm.sup.2. Two shots are applied to each palatine tonsil and two shots are delivered to the back of the tongue. In each case, light output head 16 is advanced into position with brushes 54 closely adjacent to or touching the target tissue. The procedure is repeated twice a week for six weeks. At the end of the treatment period little, if any halitosis can be detected.

FIG. 15 of U.S. Pat. No. 7,544,204 and included herein as FIG. 15, shows an embodiment of a treatment system according to the invention complete with a power supply, in use treating a patient. The system includes a power supply 320 shown as a "black box" which is suitable for powering the described pulsed xenon arc flashlamp embodiments of the invention, such power supplies being per se known to those skilled in the art. Power supply 320 can comprise a pulse-forming network, employing high voltage capacitors and inductors, or other suitable circuitry, and a connection for a utility power supply. If desired, a battery, preferably rechargeable, may be included for standby or portable use. The output pulse has characteristics suitable for energizing flashlamp 200 or 300 including suitable pulse energy and duration and high voltage peaks. Suitable peak voltages can be as known to those skilled in the art and may be in the range of about 1 to about 20 KV, being for example from about 5 to about 10 KV. Depending upon the particular light-emitting device employed, other suitable voltages may be used.

An insulated flexible power cord 322 can carry the power output from power supply 320 to a hand piece such as hand piece 324, which is here shown as an integral one-piece unit from which power cord 322 may be detached, if desired. Alternatively, hand piece 324 can be permanently secured, e.g., by molding, to power cord 322.

Hand piece 324 includes a suitable, manually grippable portion 326 and a flashlamp head 328 containing or supporting a flashlamp, which may be substantially as described with reference to FIGS. 9-13 of U.S. Pat. No. 7,544,204 and also included herein as FIGS. 9-13, subject to variation as described herein, or as will be apparent to those skilled in the art. A conveniently operable switch such as a pressure pad or button 330 is provided to enable the practitioner to activate the instrument as desired. Switch 330 can take many forms, for example mechanical pushbutton, pressure pad, heat sensor and the like, as may be desired.

Conductors 331 carry the high voltage from power unit 320 to flashlamp 300, as described above. Hand piece 324 can have an exterior form that is curved and smoothly contoured to be ergonometric and easily and comfortably manipulated by the practitioner. A slim fingerlike configuration enables hand piece 324 to be inserted into the mouth and properly located to treat the back of the tongue.

Power unit 320 can have user-settable controls to provide a desired photothermal output enabling the operator to choose from a number of available selections of pulse energy, pulse duration, number of pulses and so on. The number of selections can be for example from 2 to about 10 or may be continuously variable. Preferably, an electronic display is provided to give a visual indication of the settings. Also, power unit 320 may provide a number of treatment selections each representing a particular combination of pre-set output characteristics suitable for a particular purpose, for example, for treating a specific bacterial strain, a specific patient condition a particular halimeter reading or other suitable parameters. The programming of same can be managed by a microprocessor and suitable software if desired.

Such a system can give the practitioner a "one-touch" dosage, which could include several energy pulses of selected character, for a particular diagnosed patient condition or parameter to be treated. Such a computerized power unit or other suitable control unit, could be end-user programmable employing removable compact flash cards or other suitable data storage volume or the like. It will be understood that such a computerized power unit may be employed with any of the embodiments of the invention described herein and could be built in or integral with the handpiece or could be pluggably connectable therewith to provide an integral unit.

In use, prior to a treatment, the practitioner can, if appropriate, select a suitable data storage volume containing desired treatment configuration data, load same to the computerized power unit, and make one or more program selections to configure the treatment device to generate an energy dosage having parameters appropriate for the patient to be treated, in response to one or more manual actuations of an actuator such as a button.

As an alternative to the use of an incoherent light source such as the pulsed photothermal flash lamp described hereinabove, a laser light source may be employed. In one embodiment the laser source is tuned to a peak bacterial absorption wavelength which may correspond with the natural or artificially stained or otherwise induced color of the target bacteria. Preferably, a specific applied wavelength, or waveband is selected for each organism or group or class of organisms to be treated. Thus, the source can be attuned to the target.

Colorless bacteria may be colored to enhance absorption of lethal energy doses by staining the target area, and bacteria resident in the target area, with a suitable stain, for example a blue or a pink stain. Green stains, such as indocyanine green (ICG) are also used. The laser wavelength can then be selected to be in the waveband complementary to the color of the stain, for example blue-green for a pink stain or yellow-orange for a blue stain, light energy having a complementary hue being strongly absorbed.

Black bacteria, for example *Prevotella intermedia*, absorb any wavelength and can be targeted with a particularly effective or practical wavelength, or wavelength peak, e.g., red, orange or $CO_2$.

Laser energy can be brought to the treatment site by any suitable means for example optical fibers. Alternatively, a laser source, e.g. one or more laser diodes, can be distally mounted in, on or near the treatment head, for example in place of the distally mounted flashlamp 200 or 300 described with reference to FIGS. 9-14 of U.S. Pat. No. 7,544,204 and included herein as well as FIGS. 9-14. A laser source can be employed for spot treatments or for treatment of precisely defined targets employing pulses of duration selected to obtain the desired bactericidal result without tissue damage. In another embodiment, a cylindrical diffuser is provided to spread the laser light.

A further embodiment of the invention enhances the staining process by covalently coupling a suitable stain to an antibody to the target microorganism which acts as a vector or carrier directing the stain molecule to the target microorganism. Coupling can be effected by known methods, for example diazotization. Small dosages of antibody-coupled stain can enable great efficiency, ensuring that the stain reaches and is attached to target bacteria or other target microorganisms and can permit a reduced dosing of the patient's tissue with stain which is a visually and in other ways undesirable material. Such antibody coupling can be particularly beneficial when employed with a photodynamic stain, as described hereinbelow.

An advantage of staining or otherwise sensitizing the bacteria or other target organism is that the organism may become sufficiently sensitive to applied photothermal energy that quite brief energy pulses are effective to weaken, disable or destroy the bacteria. Suitable pulse durations may be as short as a few hundred picoseconds or from about 0.5 to 100 microseconds, e.g. about 1 microsecond or other duration in the range of about 1 to about 10 microseconds. The brevity of such energy pulses enables relatively high energy densities to be employed with low risk of damage to the ambient tissue. For example, when treating the back of the tongue, halitosis bacteria may be heated to a lethal level with little if any heating of the surrounding tissue.

Useful energy densities for such pulsed treatments of stained halitosis bacteria can be in the range of from about 0.5 to about 50 joules/$cm^2$, referring to the value of the energy density at or near the target tissue. Some embodiments of the invention can employ energy densities of from about 3 to about 20 joules/$cm^2$, for example from about 7 to about 12 joules/$cm^2$. The peak energy waveband can be selected to be at, to include, or to overlap the bacterial stain sensitization peaks, for good efficiency.

Another way to efficiently target halitosis or other bacteria or microorganisms to be treated and control risks of tissue damage or other adverse reactions is to sensitize the target bacteria, or ambient tissue harboring same, with a photodynamic bacterial toxin. One example of a suitable such toxin is methylene blue which, at low concentrations may be per se harmless to tissue and bacteria and which can be activated, for example by application of photothermal energy as described herein, to liberate a toxin which kills or weaken bacteria stained or otherwise exposed to the photodynamic toxin. The bactericidal effectiveness of methylene blue or other such photoactive chemical agents against anaerobic bacteria can be enhanced by also applying oxygen. Employment of photosensitizing agents, for example stains such as methylene blue, to color otherwise colorless microorganisms can enhance the absorption of destructive visual energy wavelengths. The lethality of the energy application may thus be enhanced, whether or not the stain liberates toxic agents, as is described in more detail below.

To this end, in another aspect the invention provides a novel tissue treatment system wherein both fluid and optical delivery systems are mounted in a single combination hand piece. The combination handpiece can comprise the addition of a, or a side-by-side pair of thin spray tubes each of which is optionally equipped with a suitable nozzle, to any of the treatment devices described herein, enabling a small liquid spray to be applied to the target surface. Desirably, the spray tubes are aligned with the optical head so that fluid and electromagnetic energy are directed to the same target site. The spray tubes can have an adjustable orientation relative to the optical head and may have adjustable or interchangeable nozzles to provide a selection of spray patterns. A rinsing tube can also be provided, if desired.

Photodynamic toxins such as methylene blue or a variety of other treatment fluids can be dispensed, as will be apparent to those skilled in the art, for example, bacterial stains, local anesthetic gels, or lower viscosity, sprayable equivalents thereof, and any other fluids described herein.

The optical delivery system is preferably configured to operate at wavelengths suitable for activating photodynamic compounds and may for example comprise a .about.760 nm diode or a lamp filtered to a waveband which activates methylene blue or at another wavelength suitable for a different photodynamic toxin which can be activated in situ with photic or thermal or photothermal energy.

In another embodiment of the invention, the combination applicator may optionally include an oxygen supply tube to provide oxygen to the target site to enhance the in situ activation of methylene blue, and optionally in addition, a rinsing tube.

In a further embodiment of the invention, the combination applicator may include an oxygen supply tube to enhance the in situ activation of the photodynamic toxin.

Methylene blue is a photodynamic stain which is not harmful to tissue and which may be employed in the invention. Methylene blue converts into a toxic compound when irradiated with light at specific wavelengths for example a 630-700 nm light source or a UVA 340-380 nm source. Methylene blue activates tissue and ambient oxygen and converts it into a free radical which poisons both bacteria and tissue. By attaching the stain to an antibody which is specific to and can attach to a Halitosis bacteria, staining can be rendered selective. Thus, the poisonous action of the irradiated stain can destroy bacteria while leaving the tongue or other tissue substantially unaffected or unharmed.

Methylene blue can be applied, in conjunction with photothermal bactericidal therapy, employing devices or instrumentation such as described hereinbelow or will be apparent to those skilled in the art in light of this disclosure.

The invention also includes methods and apparatus that enable the dosage or dosage protocol to be selected or adjusted according to the severity of the patient's halitosis condition. An initial step comprises detecting and quantifying the patient's oral odor for which various methods are known. The determination may be made organoleptically employing a subjective odor rating assessed by a physician or other third party smelling the breath. The determination can also be made by employing analytical techniques based upon gas chromatography, mass spectrometry, cryo-osmoscopy, or the like. Data obtained from these methods can be used to enable the practitioner to select an appropriate dosage or protocol, or may be input to a computerized control unit which determines the dosage and/or protocol according to a predetermined algorithm.

Another embodiment of the invention employs a portable sulfide monitor, for example a HALIMETER (trademark) monitor supplied by Interscan, Chatsworth, Calif. The HALIMETER (trademark) monitor can quantify the levels of VSCs in oral breath to provide a determination of the intensity of the halitosis condition. Data obtained from HALIMETER (trademark) monitor determinations can be used as described in the immediately preceding paragraph. A further embodiment of the invention comprises the use of a sulfide monitor, for example the HALIMETER (trademark) monitor, as a sensor to determine the severity of a patient's halitosis, the output of the sulfide monitor being coupled with a control system for a light-based halitosis treatment applicator, such as the inventive devices and apparatus described herein or other applicators known or becoming known to those skilled in the art, and being used to provide a displayed of otherwise presented indication of the severity to the practitioner or as a control parameter to automatically determine one or more treatment settings such as the applied energy intensity, duration or number of repetitions.

The invention also includes processes of treating halitosis which target one or more particular bacterial species identified as causative agents of the condition. Thus, the treatment parameters can be selected to be relatively more effective against the particular one or more species, while possibly being less effective against other species. The one or more species can be selected from the bacterial species set forth herein, notably in the background of the invention section of this specification, or from other relevant species as may be known or become known to those skilled in the art.

In a still further embodiment, the invention provides methods and apparatus wherein the bacterial populations at the target are quantitatively monitored by species or strain on a relative or absolute basis. The treatment protocol or dosage can then be varied according to the data obtained regarding the increase or decrease of one or more bacterial populations with time. Thus, for example, treatment may be continued until a desired low level of one or more halitosis-causing bacteria is reached or until a desired increase in level of a bacterium associated with health is reached. Such a latter bacterium is desirably one which is present in only low levels when halitosis is manifest and at higher levels in healthy, non-halitosis suffering individuals, for example *Streptococcus salivarius*. The particular species will be known to those skilled in the art, for example as described hereinabove, or may become known.

Photosensitizing Agents

As described above, photosensitizing agents such as stains may be employed to enhance the treatment process. Desirable aspects of the invention employ a combination of stain and energy dosage which is effective, of convenient duration and aesthetic. Biocompatible photosensitizing stains showing strong absorbance of one or more peak wavelengths output by the light source or other source of electromagnetic radiation are particularly useful in enhancing the efficacy of the energy treatments or in rendering lethal energy dosages that might otherwise be innocuous. However, excess and displaced stain may be problematic and unaesthetic if the stain exhibits itself to the subject after treatment, for example, after blowing their nose.

To control such problems while benefiting from the lethality and efficacy that use of a suitable stain can bring, the stain can be employed in relatively low concentrations, for example a concentration of less than 1%, referring to methylene blue. In practice, concentrations of less than 0.1%, for example 0.08% or lower, are desirable to avoid aesthetic problems over an extended time period. In general, again referring to methylene blue, some useful microorganism lethality can be obtained with concentrations of 0.01% or greater, although extended energy exposures may be necessary at such concentrations. Some particularly useful embodiments of the invention employ concentrations of methylene blue in the range of from about 0.02 to about 0.08%. Concentrations of methylene blue in the range of from about 0.03 to about 0.06% are also believed to be particularly effective. It will be appreciated that other stains may employ different concentrations according to their efficacy as known or as determined by routine experimentation.

The invention provides an embodiment of low dosage treatment method and composition wherein a photosensitizer is employed in micromolar concentrations, in combination with non-ionizing photic radiation including at least one intensity peak in the orange-red wavelength range of from about 500 to about 700 nm. Pursuant to the invention it has been discovered that dosages of both photosensitizer and photic radiation when used in combination may be sufficiently mild to avoid damaging healthy tissue or causing pain or discomfort while the combination is effective to combat target microorganisms. For example, molar concentrations of less than about 100 micromole (".mu.M") can be effectively employed as broad spectrum antimicrobial treatments of target surfaces, as described herein, and as selective treatments not only against Gram-positive bacteria, but also against Gram-negative bacteria. One useful range of dye photosensitizer concentration that may be employed is from about 1 to about 50.mu.M. Another is from about 1 to about 20.mu.M. Concentrations of less than about 1.mu.M, down to about 0.1.mu.M may be effective under some conditions. In one embodiment, the invention employs a low or the minimal effective dosage of stain which is sufficient to obtain a useful or desired reduction of harmful microbes. Optionally, the dosage may be selected to leave a residual population, perhaps 10 or 20% to promote the proliferation of healthy microflora.

Such modest stain concentrations may be relatively aesthetic, providing only moderate, or short-lasting coloration, yet have little, if any lethal effect when used alone. However they can provide a surprising enhancement of the efficacy of the energy treatment, reducing the effective dosage and thence the risks of physiological damage or the treatment duration.

Some photosensitizers of particular use in the practice of the invention are dyes or stains which are phototoxic to the target microorganism or microorganisms. Some specific photosensitizers which may be used in practicing the invention, in addition to methylene blue include dimethyl methylene blue, other dyes and photosensitizing compounds such for example as: photosensitizers selected from the group consisting of new methylene blue, arianor steel blue, toluidine blue, tryptan blue, crystal violet, azure blue cert, azure B chloride, azure 2, azure A chloride, azure B tetrafluoroborate, thionin, azure A eosinate, azure B eosinate, azure mix sicc., azure II eosinate, haematoporphyrin HCl, haematoporphyrin ester, aluminum disulfonated phthalocyanine, pyronin Y, neutral red and chlorines, indocyanine green (ICG) and other green stains and green dyes. Other photosensitizing agents may also be used, as will be apparent to those skilled in the art, for example, suitable biocompatible oxidizing agents such as dilute hydrogen peroxide and other stains such as phenothiaziniums, porphryins and phthalocyanins.

One useful criterion for selecting photosensitizers for use in the practice of the invention is that of having a relatively low minimum lethal dosage concentration for organisms exposed to suitable light, notably, light having a peak intensity at wavelengths overlapping with a photosensitizer absorption peak. Another useful criterion is the dark-to-light ratio of minimum lethal dosage concentration which expresses the photoactivation properties of the photosensitizer, being the ratio of the minimum concentration required to provide a dosage lethal to a given organism in darkness to the lethal concentration when illuminated. Some dyes or stains that require a fairly high minimum in darkness, may nevertheless be relatively innocuous to the target anatomy and/or commensal organisms that are natural residents of the target site when healthy. If they display a significantly enhanced activity when suitably illuminated, they may be useful in the practice of the invention. Such usefulness may be suggested by a dark-to-light ratio of minimum lethal dosage of at least 2, desirably at least 3, and more desirably 4 or more. Some useful photosensitizers may exhibit still higher ratios of 7 or 8 or more.

Some photosensitizers are less effective against gram-negative bacteria which have a protective outer membrane containing an additional membrane layer which may hinder the uptake of photosensitizing molecules. Accordingly, the invention includes embodiments employing one or more photosensitizers to treat target sites infected with gram negative bacteria, to control the gram negative bacterial population, which sensitizers are selected from the group consisting of methylene blue, dimethyl methylene blue, new methylene blue, toluidine blue, pyronin Y, neutral red and other dyes or stains known or discovered to be effective photosensitizers for gram negative bacteria.

Desirably, photosensitizers such as the haematoporphyrins which are not well taken up by Gram negative organisms, if selected for use, are employed in treating microorganism colonies that are rich in Gram positive bacteria. Various dyes such, for example, as aluminum disulfated phthalocyanine, toluidine blue, azure B chloride or methylene blue can, without limitation, be employed for treating Gram negative organisms. In embodiments of the invention practiced utilizing an HeNe laser desirably, tryptan blue or crystal violet are not employed.

Some useful combinations of photosensitizer agent and light wavelength include toluidine blue irradiated with optical or photothermal energy including a peak or peaks at or near a wavelength of about 630 nm and aluminum disulfonated phthalocyanine irradiated with optical or photothermal energy including a peak or peaks at or near a wavelength of about 660 nm.

The potential efficacy of different treatments and treatment means may be determined in simple tests, for example as described in the following Example 2:

EXAMPLE 2

Determination of Lethal Sensitization of Oral Pathogens

Suitable stain dosages for providing lethal sensitization of oral pathogens are determined in vitro by the following procedure. An objective is to determine the minimum duration of light exposure and minimum agent dilution required to achieve at least a 50% reduction in bacteria counts. Experimental tests are performed on two common pathogens using a continuously working, high intensity, red filtered halogen lamp. Red light from the filtered halogen lamp is transmitted through a flexible light guide to radiate downwardly onto petri dishes containing samples of live bacteria of species *Porphyromonas Gingivalis* and *Prevotella Intermedia* using the protocols described below. Bacteria. *Prevoltella Intermedia* is isolated from patient sample material, identified in the laboratory using standard diagnostic test systems (Remel Inc., Lenexa, Kans., USA) and is maintained by twice-weekly subculture in thioglycollate medium (Becton Dickinson and Co, Sparks, Md., USA). *P. gingivalis* ATCC 33277 obtained from Remel Inc., is maintained by a twice-weekly subculture on CDC anaerobe blood agar (Becton Dickinson and Co, USA) and in thioglycollate medium (Becton Dickinson and Co, USA). Light Source. The source for light energy is a continuously working, high intensity halogen lamp having a built-in 250-Watt quartz halogen light source, model I-250 supplied by Medithon, New York, N.Y., USA. Such lights are customarily employed for ear, nose or throat procedures. The light is transmitted through a flexible light guide and filtered to maintain maximum energy output at wavelengths in the vicinity of about 650 nm using a broadband red filter (Edmund Optics Inc., Barrington, N.J., USA). The light output power density measured at 3 cm distance from the end of the light guide with filter is about 50 milliwatts/cm2. Photosensitizer. 1% methylene blue solution (Faulding Pharmaceutical Co, Paramus, N.J., USA) is used as a photosensitizer. Serial dilutions with water of initial solution with respective concentrations of 0.1%, 0.075%, 0.05%, 0.025% and 0.01% are prepared from the initial solution using sterile 10-ml bottles of normal saline and sterile syringes. Lethal photosensitization of *P. Intermedia*. Petri dishes containing CDC anaerobe blood agar (Becton Dickinson and Co, USA) are inoculated with 0.5 ml of broth containing $5.times.10.sup.5$ CFU/ml and left closed at room temperature for about 10 minutes to let the broth penetrate the agar media. The inoculated plates are then exposed to 1 ml of methylene blue solution at concentrations 0.1%, 0.075%, 0.05%, 0.025% and 0.01% respectively for at least 60 seconds and then exposed to the red filtered light source for time intervals of 1 min, 5 min, 10 min and 20 min respectively. Only plates with concentrations of 0.01%, and 0.025% are used in the experiment with 20 min light exposure. Four plates are used for each experiment. Four inoculated plates that are not exposed to methylene blue or to the light source are used as controls. The controls are covered to protect them from ambient light. In order to examine the ability of light to cause killing of bacteria, inoculated plates are exposed to the red-filtered light at the same time intervals, without previous exposure to methylene blue, in the same groups of four plates. To study the ability of methylene blue alone to induce bacterial death, groups of four inoculated plates are exposed to the methylene blue solution at specified concentrations without subsequent exposure to the red-filtered high intensity light. A total of 108 subcultures is used for the experiment. Plates are incubated in anaerobic conditions in the jars using anaerobic pack kits (BBL GasPak Plus, Becton Dickinson and Co, Sparks, Md., USA) at 37.degree. C. for 24 hours. Samples of the resulting culture growth are taken from each plate with sterile 1:L standard loop, dispensed in 1 ml of sterile NS and placed at the same media. Cultures are incubated at anaerobic conditions at 37.degree. C. for another 24 hours, and after that the resulting colony count is performed on each plate. Lethal photosensitization of *P. Gingivalis*. Serial dilutions of the *P. gingivalis* culture are prepared from the initial culture preserved on plates using 1:L sterile standard loop (Becton Dickinson and Co, USA) and sterile NS. A Vitek calorimeter (Hach Company, Loveland, Colo., USA) is used to achieve a final concentration of about $5.times.10.sup.3$ CFU/ml from an initial 0.5 standard McFarland suspension of $10.sup.8$ CFU/ml. Plates containing CDC anaerobic blood agar (Becton Dickinson and Co, USA) are inoculated with the resulting suspension using sterile 10:L standard loops (Becton Dickinson and Co, USA). The plates are then exposed to the methylene blue solution at different concentrations and thereafter to the red-filtered high-intensity light source at different time intervals using the algorithm described for *P. Intermedia*. Plates are also incubated at 37.degree. C. in the tightly closed jars supplied with anaerobic pack kits (BBL GasPak Plus, Becton Dickinson and Co, USA) for 24 hours, and the resulting colony count is performed on each plate.

Typical results obtainable from experiments such as those described in Example 2 are shown in Table 1 below, which describes the data as the means of four values, two each from each species, along with their standard deviations. The results for the two species were broadly comparable. Statistical analyses can be carried out using single-factor analysis of variance.

TABLE 1

Survival of Bacteria Exposed to Blue Stain and Red Light
Percent of Living Bacteria

| Methylene | Exposure to Red Light | | | | |
|---|---|---|---|---|---|
| blue % | 0 | 1 min | 5 min | 10 min | 20 min |
| 0 | N/A | 70 +/− 6 | 75 +/− 7 | 73 +/− 8 | N/A |
| 0.01% | 70 +/− 11 | 73 +/− 6 | 69 +/− 7 | 55 +/− 6 | 51 +/− 4 |
| 0.025% | 75 +/− 14 | 67 +/− 4 | 47 +/− 6 | 48 +/− 8 | 49 +/− 5 |
| 0.05% | 68 +/− 12 | 53 +/− 10 | 32 +/− 7 | 32 +/− 9 | N/A |
| 0.075% | 51 +/− 10 | 45 +/− 5 | 26 +/− 5 | 25 +/− 5 | N/A |
| 0.1% | 35 +/− 9 | 39 +/− 12 | 28 +/− 9 | 24 +/− 4 | N/A |

Column 1 of Table 1 reports the concentration of stain employed in each culture as a percent of methylene blue, "methylene blue %". The remaining column headings describe the duration of red light exposure in each test.

Results. It may be seen from the data in Table 1 that a statistically significant reduction in bacterial colony count, with a survival rate of 50% or less can be achieved at concentrations of methylene blue of 0.05% and higher when the red light exposure is 10 or 20 minutes. No statistically significant difference is noted between the exposure for 10 and 20 minutes in either species or with any concentration of methylene blue. Exposure of both cultures to red-filtered high-intensity light source may produce statistically significant increased killing with duration as read at the time intervals of 1 min, 5 min and 10 min, with methylene blue concentration of 0.05%, and at the time intervals of 5 and 10 min with methylene blue concentration of 0.025%. Methylene blue concentrations of 0.075% and 0.1% show significant bactericidal effect even without light exposure. Some statistically significant bacterial killing can also be at a 0.01% concentration without light exposure in the *P. gingivalis* culture. With light exposure for 1 min both 0.075% and 0.1% concentrations of methylene blue produced statistically significant bacterial count reduction in both cultures. Little, if any statistically significant reduction in bacterial counts is noted with the exposure of either culture to the red-filtered high-intensity light source without the exposure to methylene blue.

CONCLUSION

The results of the study show that red-filtered high-intensity light, used in combination with methylene blue solution at a concentration of 0.01% or higher, can produce a bactericidal effect on both species examined, when a time of exposure less than 10 minutes and an accumulated energy level of 30 J/cm.sup.2 are employed. Significant reduction in bacteria counts can also be achieved with combination of light exposure for 5 min and methylene blue concentration of 0.025% and light exposure for 1 min and methylene blue concentration of 0.05% and higher. Methylene blue can produce bactericidal effect on *P. gingivalis* at concentration of 0.1%. Exposure to red light with wavelength of 650 nm alone does not appear to produce significant killing of *P. intermedia* or *P. gingivalis*.

Furthermore, as may be seen from the data in Table 1 that a desired level of lethal photosensitization, namely killing of 50% or more of the bacteria population, of the studied oral pathogens can be achieved under the following conditions: 1. Illumination with red halogen light for 5 minutes or more using 0.05% methylene blue stain; or 2. Exposure to red halogen light for 20 minutes in the presence of a concentration of 0.025% or 0.01% methylene blue stain.

It may be understood that some useful conditions to avoid tissue damage and destruction of commensal organisms, while obtaining useful kill rates of target bacteria are, for example, 8-12 min at 0.01%, 4-6 min at 0.025% and equivalent combinations of concentration and exposure.

The useful conditions that are apparent from Table 1 and the accompanying discussion can be understood to be exemplary of a range of possible effective conditions that may be apparent, or may be determined with modest experimentation, and which may vary according to the particular stain employed, the prevalent species of microorganism and the wavelength and energy density of the applied light. For example, it is contemplated that use of a pulsed xenon photothermal light source as described herein can significantly reduce the exposure periods required for desired lethality.

Neither exposure to the halogen light for 20 minutes in the absence of a photosensitizer, in this case methylene blue, nor concentrations of methylene blue of 0.001% or 0.025%, without halogen light, appeared to be effective in killing bacteria.

Reduction of bacteria treated with 0.05% methylene blue alone, without exposure to light, is found to be insignificant. However, concentrations of 0.075% and 0.1% methylene blue are found to be significantly bactericidal, for the test species, even in the absence of red halogen light.

The data shows that lethal photosensitization of two common oral pathogens can be obtained employing high intensity red-filtered halogen light in the presence of dilute methylene blue verifying the value of chemical photosensitization and suitable applied light as a treatment alternative to chemical antibiotics which may induce resistance. Though not demonstrated by the tests described here, unlike chemical antibiotics, combinations of halogen light and suitable stains may also destroy non-bacterial organisms such as fungi and viruses.

Mapping and Diagnostic Tongue Software Application

Figure 7A:
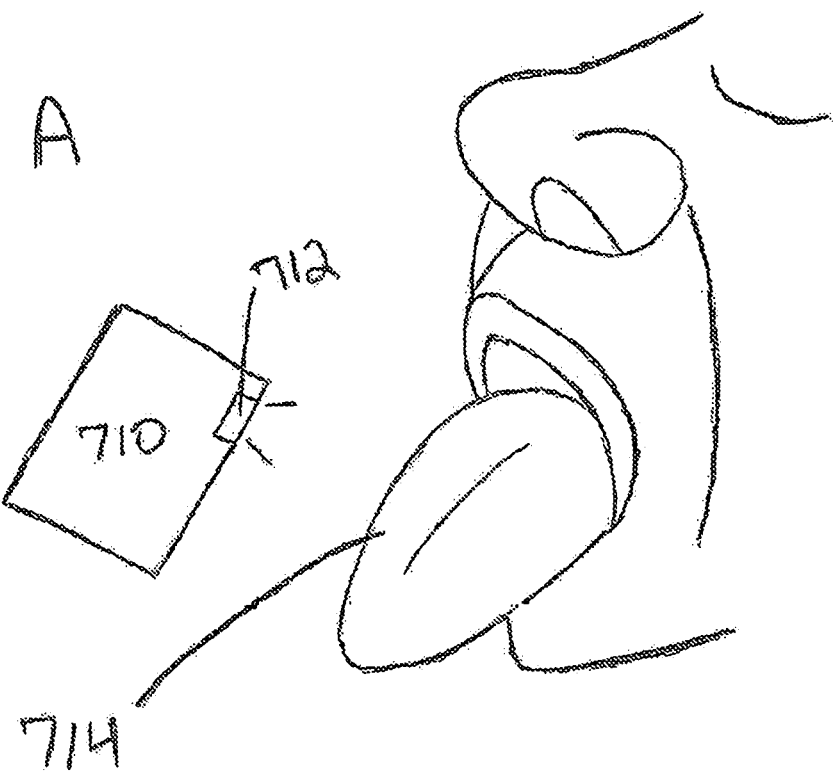
FIGS. 7A and 7B illustrate using an image of a tongue for diagnosing and mapping biofilm on a surface.
Figure 7B:
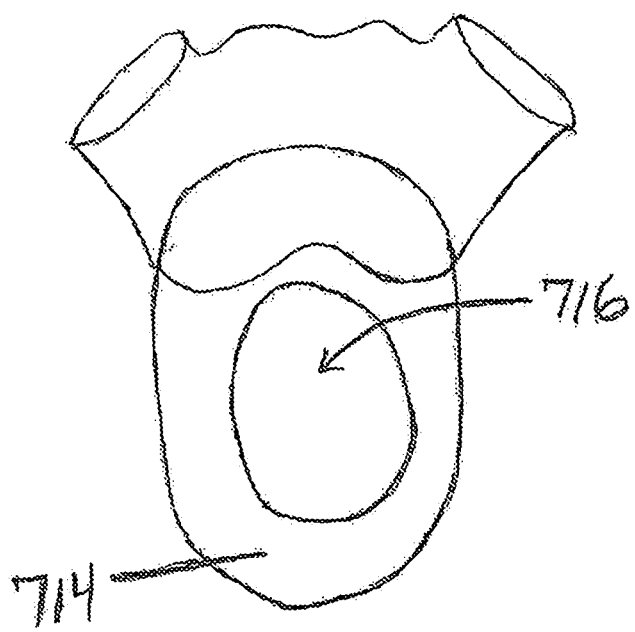

Referring now to FIGS. 7A and 7B, there is shown an imaging application for use with the present invention. The imaging application may include a smart phone or tablet application which allows for analysis of the localized presence as well as the severity of a bio-film on a surface. For example, an image of the surface of the tongue 714 may be taken, (or other areas previously disclosed), such as by a camera 712 on a smart phone or tablet 710 or other device. In FIG. 7B, the image of a tongue 714, with an affected area 716, is taken and uploaded to the software application. As shown in FIG. 8, the software application 720 produces an image 722 of the tongue. The affected area 716 from FIG. 7B is color coded or mapped by the software application based on the severity of the bio-film at each location on the surface of the tongue. For example, affected area 724 is color coded or mapped as a different color than a second section 726 of affected area in FIG. 8. These affected areas 724 and 726 can be indicated by circling or highlighting the image allowing for diagnosis of the bio-film concentration.

From the affected areas, a value is calculated across the captured image against the average color of the region. The average color is classified into a category of bio-film density that is then weighted into the image divided by 100 parts and each part weighted against the average color. The median value of this dissection gives the Tongue Health Status that will be referred to as THS score. The THS score is saved with the image. The THS score is a unique value and is as helpful indicator of overall health of the tongue, similar to other data points people track such as weight, blood pressure and glucose. The THS score is a new and unique value that will have immense value to the patient in measuring overall tongue health and to the practitioner in tracking the effectiveness of treatment.

The THS can be kept on a personal mobile device, file, computer, or in a popular health application (for example APPLE™ Health Kit™ or Google's Google Fitness™).

The THS value is broken down into 5 grades:
Tongue Health Status
(Grading for Tongue Biofilm Coating)

GRADE 1—Totally pink and moist tongue, smooth surface, no fissures, no patches, very short papilla.

GRADE 2—White coating around mid-portion of tongue (less than 25-50%), fair moisture, swallow center fissures GRADE 3—Extensive white coating of center of tongue (less than 50-75%), deep longitudinal center fissures and small patches, thick saliva, long papilla GRADE 4—White tongue (75% or more) except the tip, deep grooves and fissures, multiple patches (geographic tongue), very thick and glue-like saliva, minimal or no moisture.

GRADE 5—Brown or black tongue (hairy tongue), severe dryness, almost no saliva, very thick coating, deep grooves and long papilla, multiple patches (geographic tongue)

This is a novel and unique way to keep track of a person's overall tongue health and to track the effectiveness of treatment. The applications can correctly analyze multiple images overtime and advise whether a current treatment is effective or not. This analysis will have great impact on medical expenditures to solving biofilm coating.

The images have educational, diagnostic, and treatment uses for both the individual patient and medical practitioner. Treatment with the instrument of the present invention can be performed according to the mapping. Additional images after treatment or treatment stages can be taken to determine the effectiveness of the treatment, creating a medical record of before, after, an ongoing treatment images.

Staining of bacteria to enhance the photolytic action while useful in many embodiments, is not essential, but can be employed if desired. It is a feature of some embodiments of the invention that they may be effectively practiced to control unstained microorganisms. Employment of combined heat and light energy, pursuant to the invention, provides the unexpected benefit that elevating the target temperature may accelerate the photolytic reactions enhancing the bactericidal efficacy of the treatment.

If desired, the halitosis treatment methods and apparatus of the invention may be augmented by treating the target surfaces with one or more chemical or pharmaceutical anti-infective agents which may be administered in any suitable manner, for example by spray, drops or vapors, as an aerosol, or optionally with the assistance of a nebulizer. Suitable agents, dosages and administration methods and devices are known to the art. For example, some are described in Osbakken et al. U.S. Pat. No. 6,576,224, the disclosure of which is hereby incorporated herein by this specific reference thereto. Those skilled in the art will be able to select suitable or especially useful such an anti-infective and an administration method and device in light of the disclosure herein. Such adjunctive treatment may be effected at any appropriate time in relation to the light-utilizing therapy, for example immediately prior thereto, from 1 to 6 hours prior thereto and/or on an ongoing basis, daily, twice daily or more frequently, between light-based treatments.

Though described in relation to the treatment of non-dental target sites in the upper respiratory tract, it will be understood that the principles of the invention can be applied to the treatment of target sites, and especially mucous tissues, in other externally accessible bodily cavities including the nasal and sinus cavities in the sin-nasal tract.

Treatment of nonhuman mammals. While the invention has been described in relation to the control of microorganisms in non-dental cavities of the upper respiratory tract in humans, it will be understood that the principles of the invention can also be applied to nonhuman mammals including for example, horses, cattle, sheep and other husbanded animals, pets such as dogs and cats, laboratory animals for example mice, rats and primates, animals employed for sports, entertainment, law enforcement, draft usage, zoological or other purposes.

Dental Sites of Treatment. In addition to treatment of the described non-dental cavity sites, the invention can be applied to the treatment of other bodily sites, if desired, including for example, dental and periodontal sites. One embodiment of the invention includes the treatment of deep periodontal pockets identified as being locations of halitosis-causing bacteria by the methods, instruments, devices or apparatus of the invention as described hereinabove.

Disclosures Incorporated. The entire disclosure of each and every United States patent and patent application, each foreign and international patent publication, of each other publication and of each unpublished patent application that is referenced in this specification or elsewhere in this patent application, is hereby incorporated herein, in its entirety, by the respective specific reference that has been made thereto.

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

What is claimed is:

1. A device for removal of bio-film from non-dental tissue without cutting or injury to tissue consisting of:
   an elongated and flexible member having a first end and a second end with a downward curved section approaching the second end; said elongated member having an axial plane and said downward curved section is adjusted by bending the elongated member at a first location at an angle of 30 to 45 degrees from the axial plane of the elongated member; said downward curved section of said elongated member capable of having length and location altered by bending said elongated member at a second location;
   the first end of said elongated member connected and inserted into a fastener attachment at a first end of the fastener attachment;
   said fastener attachment having a second end for connection to a handle grip by inserting said fastener attachment into said handle grip, and receiving an energy supply and laser energy connected into and delivered through said handle grip from an external source; said fastener attachment consisting of a replaceable single element which is a separate element from said elongated flexible member and said handle grip;
   said elongated flexible member is a hollow sheath encasing a fiber optic piece for the length of the elongated flexible member;
   a fiber optic tip of said fiber optic piece protruding from the second end of the elongated member from which treatment visible light energy emits; and a lens placed on said fiber optic tip to provide a light spot size range of approximately 0.5 millimeters to 4 millimeters to a non-dental target tissue site;
   said fiber optic tip enclosed in a hollow diffuser piece fastened onto the second end of the elongated flexible member to form a light output head of the device;
   said diffuser piece allows said light energy to emit from an open bottom of the diffuser piece and for use in delivering said visible light energy to said non-dental target tissue site;
   said non-dental target tissue site selected by a user of said device from the group consisting of the back of the tongue, a tonsil, multiple tonsils, sinus area, the throat and pharynx of a subject presented with a symptom of bio-film, the non-dental target tissue site being determined to harbor a colony of anaerobic microorganisms generating malodorous gas wherein the visible light energy is applied to the non-dental target tissue site at a wavelength and an intensity and for a duration effective to control the colony of microorganisms; and applying to the non-dental target tissue site longer wavelength energy comprising heat, RF or microwave energy or combinations of two or more of said energies.

2. The device according to claim 1, wherein the heat energy is provided by an infrared radiative source, a convective source, a conductive source or by in situ induction by RF or microwave energy.

3. The device according to claim 1, wherein the RF energy is in a range of from about 300 kHz to about 100 MHz.

4. The device according to claim 3, wherein the RF energy has an output power of from about 5 to about 200 W, a pulse duration of from about 1 to about 500 msec and a pulse rate of from about 0.1 to about 10 pulses per second.

5. The device according to claim 1, wherein the microwave energy has a frequency or frequencies in the range of from about 100 MHz to about 50,000 MHz.

6. A method for removal of bio-film from non-dental tissue without cutting or injury to tissue comprising:
   selecting a non-dental target tissue site of a patient, said non-dental target tissue site selected from the group consisting of the back of the tongue, a tonsil, multiple tonsils, sinus area, the throat and pharynx of a subject presented with a symptom of bio-film, the non-dental target tissue site being determined to harbor a colony of anaerobic microorganisms generating malodorous gas;
   disrupting said non-dental target tissue site with a plasma effect by a power wash of laser pulses, water and air at said non-dental target tissue site to cause cavitation at said non-dental target tissue site;

placing a device at location in proximity to said non-dental target tissue site; said device having an elongated and flexible member having a first end and a second end with a downward curved section approaching the second end, said downward curved section having a first length and location on said elongated flexible member; said downward curved section of said device is adjusted by bending the elongated flexible member at an angle of 30 to 45 degrees from the axial plane of the elongated flexible member;

the first end of said elongated flexible member connected and inserted into a fastener attachment at a first end of the fastener attachment;

said fastener attachment having a second end for connection to a handle grip by inserting said fastener attachment into said handle grip, and receiving an energy supply and laser energy connecting into and delivered through said handle grip from an external source; said fastener attachment consisting of a replaceable single element which is a separate element from said elongated flexible member and said handle grip;

said elongated flexible member is a hollow sheath encasing a fiber optic piece for the length of the elongated flexible member;

said fiber optic piece having a fiber optic tip protruding from the second end of the elongated flexible member from which treatment visible light energy emits; and a lens placed on said fiber optic tip to provide a light spot size range of approximately 0.5 millimeters to 4 millimeters to said non-dental target tissue site;

said fiber optic tip enclosed in a hollow diffuser piece fastened onto the second end of the elongated flexible member to form a light output head of the device; said diffuser piece having an open bottom;

emitting visible light energy from said open bottom of said diffuser piece;

delivering said visible light energy to said non-dental target tissue site;

applying said visible light energy to the non-dental target tissue site at a wavelength and an intensity and for a duration effective to control the colony of microorganisms.

7. The method according to claim 6, further comprising:
applying to the non-dental target tissue site longer wavelength energy comprising heat, RF or microwave energy or combinations of two or more of said energies.

8. The method according to claim 7, wherein the heat energy is provided by an infrared radiative source, a convective source, a conductive source or by in situ induction by RF or microwave energy.

9. The method according to claim 7, wherein the RF energy is in a range of from about 300 kHz to about 100 MHz.

10. The method according to claim 9, wherein the RF energy has an output power of from about 5 to about 200 W, a pulse duration of from about 1 to about 500 msec and a pulse rate of from about 0.1 to about 10 pulses per second.

11. The method according to claim 7, wherein the microwave energy has a frequency or frequencies in the range of from about 100 MHz to about 50,000 MHz.

12. The method according to claim 6, further comprising staining said selected non-dental target tissue site to enhance absorption of said light energy.

13. The method according to claim 12, wherein said staining is done with an indocyanine green stain.

14. The method according to claim 6, wherein said colony of microorganisms has a count reduction of about 50%.

15. The method according to claim 6, further comprising after the applying step of the method, the step of altering said first length and location of said downward curved section of said elongated flexible member by bending said elongated flexible member at a second location, and repeating said method at least once.

16. The method according to claim 6, further comprising after the applying step of the method, the step of adjusting said downward curved section of said device by bending the elongated flexible member at a second angle of 30 to 45 degrees from the axial plane of the elongated flexible member, said second angle different than said first angle, and repeating said method at least once.

* * * * *